United States Patent [19]
Campbell et al.

[11] Patent Number: 6,143,024
[45] Date of Patent: Nov. 7, 2000

[54] ANNULOPLASTY RING HAVING FLEXIBLE ANTERIOR PORTION

[75] Inventors: Louis A. Campbell; Robert M. Casanova, both of Austin, Tex.

[73] Assignee: Sulzer Carbomedics Inc., Austin, Tex.

[21] Appl. No.: 09/090,192

[22] Filed: Jun. 4, 1998

[51] Int. Cl.$^7$ .................................................. A61F 2/24
[52] U.S. Cl. ............................................................ 623/2.36
[58] Field of Search ........................... 623/2, 900, 2.36, 623/2.37

[56] References Cited

U.S. PATENT DOCUMENTS

| | | |
|---|---|---|
| 3,656,185 | 4/1972 | Carpentier .................................... 623/2 |
| 4,602,911 | 7/1986 | Ahmadi et al. . |
| 4,917,698 | 4/1990 | Carpentier et al. . |
| 5,041,130 | 8/1991 | Cosgrove et al. . |
| 5,061,277 | 10/1991 | Carpentier et al. . |
| 5,201,880 | 4/1993 | Wright et al. . |
| 5,258,021 | 11/1993 | Duran . |
| 5,306,296 | 4/1994 | Wright et al. . |
| 5,350,420 | 9/1994 | Cosgrove et al. . |
| 5,415,667 | 5/1995 | Frater ...................................... 623/2.11 |
| 5,669,919 | 9/1997 | Sanders et al. . |
| 5,674,279 | 10/1997 | Wright et al. . |
| 5,776,189 | 7/1998 | Khalid ........................................ 623/2 |
| 5,824,066 | 10/1998 | Gross .................................... 623/2.36 |

*Primary Examiner*—David H. Willse
*Attorney, Agent, or Firm*—Timothy L. Scott; Philip S. Lyren; Kenneth S. Barrow

[57] ABSTRACT

An annuloplasty ring is provided for implanting about a mitral valve. The annuloplasty ring includes a first, generally rigid section and a second, generally flexible section. The rigid section is positioned adjacent the posterior portion of a mitral valve annulus and the flexible section is positioned adjacent the anterior portion of the mitral valve annulus.

18 Claims, 1 Drawing Sheet

ANNULOPLASTY RING HAVING FLEXIBLE ANTERIOR PORTION

BACKGROUND OF THE INVENTION

The present invention relates to a support ring for use in the surgical correction of heart valve disorders.

A human heart generally includes four valves. One of these valves, the mitral valve, is located in the left atrioventricular opening and serves to prevent back flow, or regurgitation, of blood being pumped through the heart. Regurgitation can reduce cardiac output and cause other cardiac problems. Various diseases and natural defects can cause a valve to fail to operate properly and regurgitate. Dilation or deformation of the mitral valve annulus can cause regurgitation. One method of eliminating or reducing regurgitation is restoring the proper size and shape of the valve annulus in a procedure known as annuloplasty.

Annuloplasty involves the surgical implantation of a support ring about the dilated valve annulus, in this case the mitral valve annulus, restoring the natural size and shape to the annulus and allowing the valve leaflets to function normally. Since the annuloplasty technique was first implemented, several designs of the annuloplasty ring have been developed. In one of the earliest designs, a rigid ring was sewn about the valve annulus, see e.g., U.S. Pat. No. 3,656,185. Rigid rings serve the basic purpose of restoring the valve annulus to its natural shape. However, rigid rings can have several negative effects, including restricted contraction of the left ventricle.

Another annuloplasty ring design is a fully flexible ring, see e.g., U.S. Pat. No. 4,061,277. The fully flexible ring has the advantage of allowing a more normal three-dimensional movement of the tissue surrounding the valve annulus. However, a fully flexible ring generally is not able to restore the natural shape of the valve annulus and tends to be more difficult to implant. Additional annuloplasty ring designs include various partial rigid rings and rings with rigid and flexible portions, see e.g., U.S. Pat. No. 5,061,277.

Many of the partial rings and rigid/flexible rings are designed so that the rigid portion is sutured adjacent the anterior portion of the mitral valve annulus, while the posterior portion of the mitral valve annulus has no support or a flexible support. These designs tend to create the same problem known as systolic anterior motion (SAM), where the anterior leaflet of the mitral valve bulges out into the left ventricular out flow track (LVOT) causing obstruction of the blood flow into the aortic valve. Another partial ring is designed so that the partial, rigid ring is sutured adjacent the posterior portion of the valve annulus. However, when the posterior portion of the valve annulus is supported and the anterior portion has no support, the anterior portion may dilate or deform.

Therefore, there is a need for an annuloplasty ring that is easily implantable, restores the valve annulus to its natural shape, and does not induce systolic anterior motion.

SUMMARY OF THE INVENTION

The present invention is directed toward a support ring for restoring the shape of a heart valve annulus, i.e., an annuloplasty ring. Specifically, an annuloplasty ring for implantation about a mitral valve includes a first section for positioning adjacent a posterior portion of a mitral valve and a second section for positioning adjacent an anterior portion of a mitral valve. The first section has a first and a second end. The second section extends between the first and second ends of the first section, thus forming a complete ring.

The first section is generally rigid, supporting the posterior portion of the valve annulus in a desired shape. The second section is generally flexible, allowing full three dimensional motion of the heart while preventing dilation of the anterior portion of the valve annulus. In one embodiment, the first section extends generally from mitral valve commissure to commissure on the posterior portion of the mitral valve annulus, forming a generally "C" shape. The associated the second section is generally linear. Consequently, the full ring is generally "D" shaped to conform to the general shape of a typical mitral valve.

The first section includes an inner core made from titanium or other suitable biocompatible material providing the necessary rigidity to prevent dilation of the annulus. A tubular body extends the full circumference of the ring, including both the first and second sections. The tubular body surrounds the inner core of the first section. In one embodiment, the tubular body comprises a flexible, biocompatible material, e.g., silicone rubber tubing. An outer sheath surrounds the tubular body, also extending the full circumference of the ring. In one embodiment, the outer sheath is selected from the group consisting of polyester knit, PTFE knit, and ePTFE knit or other suitable tubular materials.

The present invention provides several advantages. First, the ring has sufficient rigidity for easy positioning and suturing about the mitral valve annulus. Also, the ring supports the mitral valve annulus adequately to restore its proper shape and prevent dilation. Further, the ring reduces or eliminates systolic anterior motion because the flexible anterior portion of the ring allows the anterior leaflet to open fully, bending into the left ventricular outflow track during diastolic opening, then allowing unobstructed flow through the left ventricular outflow track toward the aortic valve during systole.

DETAILED DESCRIPTION OF THE EMBODIMENTS

Figure 1:
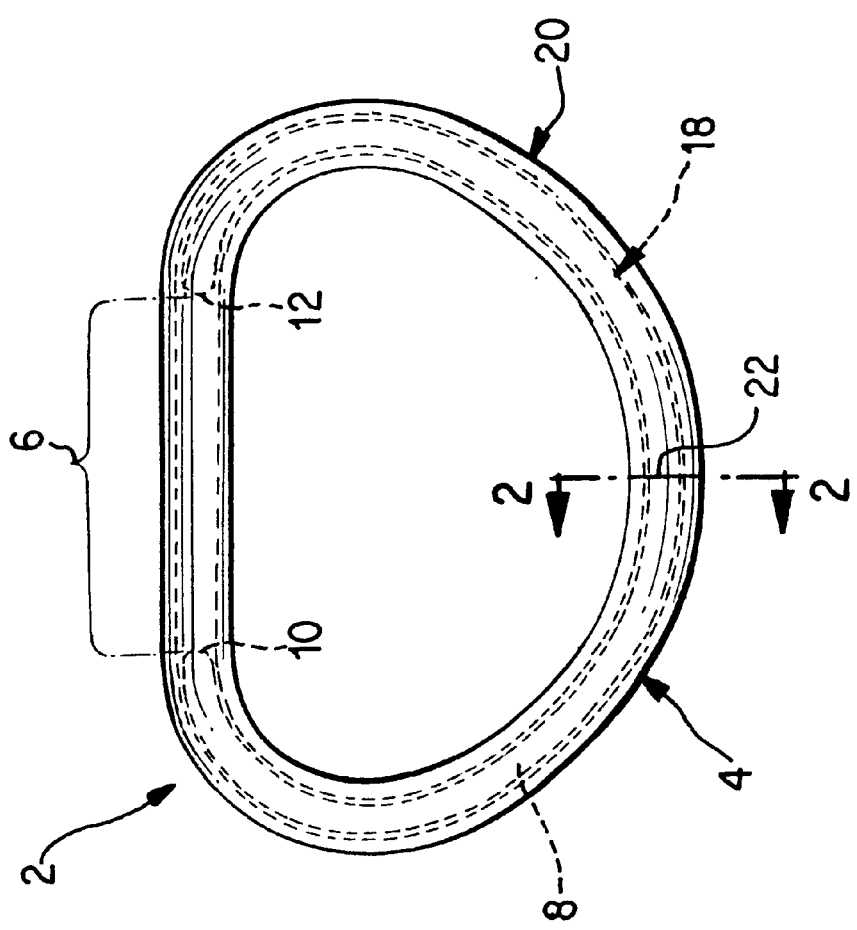
FIG. 1 is a top view of a mitral annuloplasty ring.

One embodiment of the invention is shown in FIG. 1. Mitral annuloplasty ring 2 includes a first, generally rigid section 4 and a second, generally flexible section 6. In the embodiment shown in FIG. 1, the entire ring 2 is generally "D" shaped to generally conform to the shape of a typical mitral valve annulus. In other embodiments, the ring may be of a shape suitable for the specific application, e.g., more round or oval shaped. When ring 2 is implanted, first section 4 is positioned adjacent the posterior side of a mitral valve annulus from commissure to commissure, or trigone to trigone. Consequently, second section 6 is positioned adjacent the anterior portion of the mitral valve annulus.

In one embodiment, generally rigid section 4 includes an inner core 8, which provides support for the posterior portion of the mitral valve annulus. Inner core 8 includes first end 10 and second end 12; the ends generally defining the limits of first section 4. In other words, when ring 2 is implanted, ends 10 and 12 are generally adjacent the two mitral valve commissures. Inner core 8 is fabricated from of titanium or other suitable material that provides the requisite support needed to prevent the valve annulus from dilating or deforming. Additionally, inner core 8 should be of a biocompatible material and be able to maintain its composition for an extended period of time as needed for an implantable device.

Figure 2:
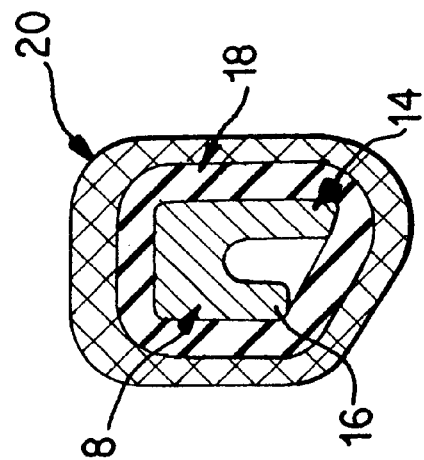
FIG. 2 is a side, cut-away view of a mitral annuloplasty ring.

FIG. 2 shows a cross-section of first section 4 of ring 2 along line A—A. In this embodiment, the cross-sectional shape of inner core 8 is generally "U"-shaped with an outer leg 14 of the "U" longer than an inner leg 16. Inner core 8 may also have other suitable cross-sectional shapes, including square, round, oval, and others. Referring again to FIG. 1, inner core 8 is in the general shape of a "C", where ends 10, 12 are curved toward each other. In other embodiments where the overall shape of ring 2 varies, the shape of inner core 8 will also vary.

As shown in FIG. 2, tubular body 18 surrounds inner core 8. As shown in FIG. 1, tubular body 18 extends the full circumference of ring 2, thereby defining a complete ring. In one embodiment, tubular body 18 is fabricated from of silicone rubber tubing. Other suitable materials may also be used. Second section 6 of ring 2 does not include an inner core; however, tubular body 18 provides some support for the anterior portion of the mitral valve annulus. Additionally, tubular body 18 provides suitable flexibility to allow the normal three-dimensional motion of the mitral valve during the systole/diastole cycle. Consequently, the mitral valve is supported primarily in the posterior portion to prevent or reduce dilation, and is also allowed suitable flexibility in the anterior portion, thereby eliminating or reducing the occurrence of SAM. Further, the general rigidity of the posterior portion of ring 2 provides a generally stable overall ring that is easier to implant than a typical flexible ring.

Referring again to FIGS. 1 and 2, outer sheath 20 surrounds tubular body 18, extending the full circumference of ring 2. Sheath 20 provides both a suitable material for suturing ring 2 to the valve annulus and a surface for promoting tissue growth with the surrounding annulus tissue. Sheath 20 may be made from any suitable biocompatible material, including polyester knit, PTFE knit, and ePTFE knit. Sheath 20 generally conforms to the outer shape of tubular body 18 and is sewn into a complete ring along seam 22.

The overall cross-sectional and circumferential dimensions of ring 2 are selected for the specific heart valve annulus. Annuloplasty rings can be sized from 24 mm to 40 mm, but are more commonly sized from 26 mm to 36 mm.

Other embodiments are within the scope of the following claims.

We claim the following:

1. An annuloplasty ring for implantation about a mitral valve having anterior and posterior portions and a plurality of commissures, said ring having a circumference and comprising:
   a generally rigid first section configured to be positioned adjacent a posterior portion of a mitral valve, said first section having a first and a second end; and
   a generally flexible second section configured to be positioned adjacent an anterior portion of said mitral valve, said second section coupled to and extending between said first and second ends of said first section and configured to allow the normal three-dimensional motion of said valve during the systolic and diastolic cycle.

2. The apparatus of claim 1, wherein said first section is configured to extend generally between two of said commissures on the posterior portion of said mitral valve.

3. The apparatus of claim 1, wherein said second section is generally linear.

4. The apparatus of claim 1, wherein said first section includes an inner core having a first end and a second end.

5. The apparatus of claim 4, wherein said inner core comprises titanium.

6. The apparatus of claim 1, said ring further comprising a tubular body extending around the full circumference of said ring, including said first and said second sections.

7. The apparatus of claim 6, wherein said tubular body comprises a flexible, biocompatible material.

8. The apparatus of claim 6, wherein said tubular body comprises silicone rubber tubing.

9. The apparatus of claim 6, wherein said ring further comprises an outer sheath surrounding said tubular body, said outer sheath extending around the full circumference of said ring.

10. The apparatus of claim 9, wherein said outer sheath is selected from the group consisting of polyester knit, polytetrafluoroethylene knit, and expanded polytetrafluoroethylene knit.

11. An annuloplasty ring for supporting a mitral valve having anterior and posterior portions and a plurality of commissures, said annuloplasty ring having a circumference and comprising:
    a generally rigid member configured to be positioned adjacent a posterior portion of a mitral valve;
    a flexible tubular member surrounding said generally rigid member and extending around the full circumference of said ring; and
    a sheath surrounding said tubular member and extending about the full circumference of said ring, wherein said flexible tubular member and said sheath are configured to permit movement of an anterior portion of the mitral valve annulus in more than one dimension.

12. The annuloplasty ring of claim 11, wherein said generally rigid member is configured to extend generally between two of said commissures on the posterior portion of said mitral valve.

13. The annuloplasty ring of claim 11, wherein said generally rigid member is C-shaped and said ring is D-shaped.

14. The annuloplasty ring of claim 11, wherein said generally rigid member comprises titanium.

15. The annuloplasty ring of claim 11, wherein said generally rigid member comprises a flexible, biocompatible material.

16. The annuloplasty ring of claim 11, wherein said tubular member comprises silicone rubber tubing.

17. The annuloplasty ring of claim 11, wherein said sheath is selected from the group consisting of polyester knit, polytetrafluoroethylene knit, and expanded polytetrafluoroethylene knit.

18. An annuloplasty ring for implantation about a mitral valve in a heart, said mitral valve having anterior and posterior leaflets for opening and closing said valve, and said heart having a left ventricular outflow track, said ring comprising:
    a generally rigid first section configured to be positioned adjacent said posterior leaflet of said mitral valve, said first section having a first and a second end; and
    a generally flexible second section configured to be positioned adjacent said anterior leaflet of said mitral valve, said second section coupled to and extending between said first and second ends of said first section and configured to allow said anterior leaflet to bend into said left ventricular outflow track during opening of said valve.

* * * * *